United States Patent [19]
Chang

[11] Patent Number: 5,888,796
[45] Date of Patent: Mar. 30, 1999

[54] CLONE OF A NUCLEOTIDE SEQUENCE ENCODING A PROTEIN HAVING TWO FUNCTIONS

[75] Inventor: Yie-Hwa Chang, St. Louis, Mo.

[73] Assignee: St. Louis University, St. Louis, Mo.

[21] Appl. No.: 40,705

[22] Filed: Mar. 18, 1998

Related U.S. Application Data

[62] Division of Ser. No. 595,025, Jan. 31, 1996.

[51] Int. Cl.⁶ .............................. C12N 9/48; C07H 21/04
[52] U.S. Cl. ........................................... 435/212; 536/23.2
[58] Field of Search ............................ 435/212; 536/23.2

[56] References Cited

U.S. PATENT DOCUMENTS

| | | | |
|---|---|---|---|
| 4,865,974 | 9/1989 | Ben-Bassat et al. | 435/68 |
| 5,470,719 | 11/1995 | Meng et al. | 435/69.1 |
| 5,608,036 | 3/1997 | Meng et al. | 530/324 |

OTHER PUBLICATIONS

Arfin et al., Cotranslational processing and protein turnover in eukaryotic cells, *Biochemistry* 27 (21):7979–7984.
Ball et al., *J. Mol Biol.* 79:531–537 (1973).
Bazan et al., Sequence and structure comparison suggest that methionine aminopeptidase, prolidase, aminopeptidase P, and creatinase share a common fold, *Proc. of the Natl. Acad. of Sci. USA* 91:2473–2477 (1994).
Ben–Bassat et al., *J. Bacteriol.* 169:751–757 (1987).
Chang et al., *J. Biol Chem.* 265:19892–19897 (1990).
Chang et al., *J. Biol. Chem.* 267:8007–8011 (1992).
Duronio et al., *Science* 243:796–800 (1989).
Gordon et al., *J. Biol. Chem.* 266:8647–8650 (1991).
Huang et al., *Biochemistry* 26:8242–8246 (1987).
Kendall et al., *J. Biol. Chem.* 267:20667–20673 (1992).
Kozak, *J. Biol. Chem.* 26:19867–19870 (1991).
Li et al., *Proc. Natl. Acad. Sci USA* 92:12375–12361 (1995).
Li et al., Molecular cloning of a human complementary DNA encoding an initiation factor–2 associated protein (p67), *Biochimica et Biophysica Acta* 1260:333–336 (1995).
Meinnel et al., Methionine as translation start signal: A review of the enzymes of the pathway in *Escherichia coli*, *Biochimie* 75:1061–1075.
Miller et al., *Proc. Natl. Acad. Sci. USA* 84:2718–2722 (1987).
Moerschell et al., *J. Biol. Chem.* 265:19638–19643 (1990).
Ngo et al., Computational complexity, protein structure prediction, and the Levinthal paradox. In: The Protein Folding Problem and Tertiary Structure Prediction, Eds. Merz et al., Birkhauser, Boston, MA 491–495 (1994).
Ray et al., *Biochemistry* 32:5151–5159 (1993).
Roderick et al., *Biochemistry* 32:3907–3912 (1993).
Wu et al., Cloning and characterization of complementary DNA encoding the eukaryotic initiation factor 2–associated 67–kDa protein (p67), *J. Bio. Chem.* 268(15):10796–10801 (1993).

*Primary Examiner*—Karen Cochrane Carlson
*Assistant Examiner*—Einar Stole
*Attorney, Agent, or Firm*—Howell & Haferkamp, L.C.

[57] ABSTRACT

A nucleotide sequence which encodes a protein which is substantially similar to eukaryotic initiation factor-2 (eIF-2) associated glycoprotein (p67) and also has methionine amino peptidase activity. The encoded protein may facilitate protein synthesis by protecting eIF-2 from phosphorylation and prepare the protein for critical cellular role by removing N-terminal methionine.

12 Claims, 3 Drawing Sheets

```
 -34                                    ctctgtctcattccctcgcgctctctcgggcaac
   1 ATGGCGGGTGTGGAGGAGGTAGCGGCCTCCGGGAGCCACCTGAATGGCGACCTGGATCCA
     M  A  G  V  E  E  V  A  A  S  G  S  H  L  N  G  D  L  D  P    20
  61 GACGACAGGGAAGAAGGAGCTGCCTCTACGGCTGAGGAAGCAGCCAAGAAAAAAGACGA
     D  D  R  E  E  G  A  A  S  T  A  E  E  A  A  K  K  K  R  R    40
 121 AAGAAGAAGAAGAGCAAAGGGCCTTCTGCAGCAGGGGAACAGGAACCTGATAAAGAATCA
     K  K  K  K  S  K  G  P  S  A  A  G  E  Q  E  P  D  K  E  S    60
 181 GGAGCCTCAGTGGATGAAGTAGCAAGACAGTTGGAAAGATCAGCATTGGAAGATAAAGAA
     G  A  S  V  D  E  V  A  R  Q  L  E  R  S  A  L  E  D  K  E    80
 241 AGAGATGAAGATGATGAAGATGGAGATGGCGATGGAGATGGAGCAACTGGAAAGAAGAAG
     R  D  E  D  D  E  D  G  D  G  D  G  D  G  A  T  G  K  K  K   100
 301 AAAAAGAAGAAGAAGAAGAGAGGACCAAAAGTTCAAACAGACCCTCCCTCAGTTCCAATA
     K  K  K  K  K  K  R  G  P  K  V  Q  T  D  P  P  S  V  P  I   120
 361 TGTGACCTGTATCCTAATGGTGTATTTCCCAAAGGACAAGAATGCGAATACCCACCCACA
     C  D  L  Y  P  N  G  V  F  P  K  G  Q  E  C  E  Y  P  P  T   140
 421 CAAGATGGGCGAACAGCTGCTTGGAGAACTACAAGTGAAGAAAAGAAAGCATTAGATCAG
     Q  D  G  R  T  A  A  W  R  T  T  S  E  E  K  K  A  L  D  Q   160
 481 GCAAGTGAAGAGATTTGGAATGATTTTCGAGAAGCTGCAGAAGCACATCGACAAGTTAGA
     A  S  E  E  I  W  N  D  F  R  E  A  A  E  A  H  R  Q  V  R   180
 541 AAATACGTAATGAGCTGGATCAAGCCTGGGATGACAATGATAGAAATCTGTGAAAAGTTG
     K  Y  V  M  S  W  I  K  P  G  M  T  M  I  E  I  C  E  K  L   200
 601 GAAGACTGTTCACGCAAGTTAATAAAAGAGAATGGATTAAATGCAGGCCTGGCATTTCCT
     E  D  C  S  R  K  L  I  K  E  N  G  L  N  A  G  L  A  F  P   220
 661 ACTGGATGTTCTCTCAATAATTGTGCTGCCCATTATACTCCCAATGCCGGTGACACAACA
     T  G  C  S  L  N  N  C  A  A  H  Y  T  P  N  A  G  D  T  T   240
 721 GTATTACAGTATGATGACATCTGTAAAATAGACTTTGGAACACATATAAGTGGTAGGATT
     V  L  Q  Y  D  D  I  C  K  I  D  F  G  T  H  I  S  G  R  I   260
 781 ATTGACTGTGCTTTTACTGTCACTTTTAATCCCAAATATGATACGTTATTAAAAGCTGTA
     I  D  C  A  F  T  V  T  F  N  P  K  Y  D  T  L  L  K  A  V   280
 841 AAAGATGCTACTAACACTGGAATAAAGTGTGCTGGAATTGATGTTCGTCTGTGTGATGTT
     K  D  A  T  N  T  G  I  K  C  A  G  I  D  V  R  L  C  D  V   300
 901 GGTGAGGCCATCCAAGAAGTTATGGAGTCCTATGAAGTTGAAATAGATGGGAAGACATAT
     G  E  A  I  Q  E  V  M  E  S  Y  E  V  E  I  D  G  K  T  Y   320
 961 CAAGTGAAACCAATCCGTAATCTAAATGGACATTCAATTGGGCAATATAGAATACATGCT
     Q  V  K  P  I  R  N  L  N  G  H  S  I  G  Q  Y  R  I  H  A   340
1021 GGAAAAACAGTGCCGATTGTGAAAGGAGGGGAGGCAACAAGAATGGAGGAAGGAGAAGTA
     G  K  T  V  P  I  V  K  G  G  E  A  T  R  M  E  E  G  E  V   360
1081 TATGCAATTGAAACCTTTGGTAGTACAGGAAAAGGTGTTGTTCATGATGATATGGAATGT
     Y  A  I  E  T  F  G  S  T  G  K  G  V  V  H  D  D  M  E  C   380
1141 TCACATTACATGAAAAATTTTGATGTTGGACATGTGCCAATAAGGCTTCCAAGAACAAAA
     S  H  Y  M  K  N  F  D  V  G  H  V  P  I  R  L  P  R  T  K   400
1201 CACTTGTTAAATGTCATCAATGAAAACTTTGGAACCCTTGCCTTCTGCCGCAGATGGCTG
     H  L  L  N  V  I  N  E  N  F  G  T  L  A  F  C  R  R  W  L   420
1261 GATCGCTTGGGAGAAAGTAAATACTTGATGGCTCTGAAGAATCTGTGTGACTTGGGCATT
     D  R  L  G  E  S  K  Y  L  M  A  L  K  N  L  C  D  L  G  I   440
1321 GTAGATCCATATCCACCATTATGTGACATTAAAGGATCATATACAGCGCAATTTGAACAT
     V  D  P  Y  P  P  L  C  D  I  K  G  S  Y  T  A  Q  F  E  H   460
1381 ACCATCCTGTTGCGTCCAACATGTAAAGAAGTTGTCAGCAGAGGAGATGACTATtaaact
     T  I  L  L  R  P  T  C  K  E  V  V  S  R  G  D  D  Y         478
1441 tagtccaaagccacctcaacacctttatttcctgagctttgttggaaaacatgataccag
1501 aattaatttgccacatgttgtctgttttaacagtggacccatgtaatactttatccatg
1561 tttaaaaagaaggaatttggacaaaggcaaaccgtctaatgtaattaaccaacgaaaaag
1621 ctttccggacttttaaatgctaactgttttccccttcctgtctaggaaatgctataaa
1681 gctcaaattagttaggaatgacttatacgttttgttttgaatacctaagagatacttttt
1741 ggatatttatattgccatattcttacttgaatgctttgaatgactacatccagttctgca
1801 cctatacctctggtgttgcttttaaccttcctggaatccatttctaaaaaataaagac
1861 attttcagatctgaaaaaaaaaaaaaaaaaaa
```

Fig. 1

```
Rat:   1 MAGVEEASSFGGHLNRDLDPDDREEGTSSTAEEAAKKKRRKKKKGKGAVS
         |||||...  |:|||  ||||||||||..||||||||||||||||:||: .
Human: 1 MAGVEEVAASGSHLNGDLPDDREEGAASTAEEAAKKKRRKKKKSKGPSA 51 AGQQELDKESGTSVDEVAKQLERQALEEKEKDDDDEDGDGDGAAGKKK
         ||:||  |||||.||||||:||||  |||:||:|:||||||||||| .||||
      51 AGEQEPDKESGASVDEVARQLERSALEDKERDEDDEDGDGDGATGKKK 101 KKKKKKRGPRVQTDPPSVPICDLYPNGVFPKGQECEYPPTQDGRTAAWRT
         ||||||||:|||||||||||||||||||||||||||||||||||||||||
     101 KKKKKKRGPKVQTDPPSVPICDLYPNGVFPKGQECEYPPTQDGRTAAWRT 151 TSEEKKALDQASEEIWNDFREAAEAHRQVRKYVMSWIKPGMTMIEICEKL
         ||||||||||||||||||||||||||||||||||||||||||||||||||
     151 TSEEKKALDQASEEIWNDFREAAEAHRQVRKYVMSWIKPGMTMIEICEKL 201 EDCSRKLIKENGLNAGLAFPTGCSLNNCAAHYTPNAGDTTVLQYDDICKI
         ||||||||||||||||||||||||||||||||||||||||||||||||||
     201 EDCSRKLIKENGLNAGLAFPTGCSLNNCAAHYTPNAGDTTVLQYDDICKI 251 DFGTHISGRIIDCAFTVTFNPKYDILLKAVKDATNTGIKCAGIDVRLCDV
         ||||||||||||||||||||||||||.|||||||||||||||||||||||
     251 DFGTHISGRIIDCAFTVTFNPKYDTLLKAVKDATNTGIKCAGIDVRLCDV 301 GEAIQEVMESYEVEIDGKTYQVKPIRNLNGHSIGPYRIHAGKTVPIVKGG
         |||||||||||||||||||||||||||||||||.||||||||||||||||
     301 GEAIQEVMESYEVEIDGKTYQVKPIRNLNGHSIGQYRIHAGKTVPIVKGG 351 EATRMEEGEVYAIETFGSTGKGVVHDDMECSHYMKNFDVGHVPIRLPRTK
         ||||||||||||||||||||||||||||||||||||||||||||||||||
     351 EATRMEEGEVYAIETFGSTGKGVVHDDMECSHYMKNFDVGHVPIRLPRTK 401 HLLNVINENFGTLAFCRRWLDRLGESKYLMALKNLCDLGIVDPYPPLCDI
         ||||||||||||||||||||||||||||||||||||||||||||||||||
     401 HLLNVINENFGTLAFCRRWLDRLGESKYLMALKNLCDLGIVDPYPPLCDI 451 KGSYTAQFEHTILCAQPVKKLSAEEMTIKT  480
         |||||||||||||  ...|.:  . :
     451 KGSYTAQFEHTILLRPTCKEVVSRGDDY    478
```

CLONE OF A NUCLEOTIDE SEQUENCE ENCODING A PROTEIN HAVING TWO FUNCTIONS

This application is a divisional of U.S. application Ser. No. 08/595,025, filed on Jan. 31, 1996.

HISTORY OF THE INVENTION

In all living cells, protein synthesis is initiated with an AUG codon. This initiation AUG codon specifies methionine in the cytosol of eukaryotes (1, 2). Eukaryotic initiation factor-2 plays a major role in this initiation event. The $NH_2$-methionine, in both eukaryotes and prokaryotes, will be removed by methionine aminopeptidases (MAPs), if the penultimate residue is small and uncharged, e.g. Ala, Cys, Gly, Pro, Ser, Thr and Val (2–5). Removal of the $NH_2$-methionine is essential for certain proteins to function normally in vivo. These proteins can be categorized into at least two groups. For the first group, the removal of the initiator methionine is required for subsequent N-terminal modifications, such as N-myristoylation, which is essential for their normal function, including signal transduction, certain cancer cell growth and protein targeting (6, 7). For the second group, the removal of the initiator methionine is required to allow the other N-terminal residues to function normally in their critical roles in catalysis. Some proteins when overexpressed in bacteria or other organisms, in which limited MAPs are available, may still have the undesired initiator methionine attached to their N-termini, and thus become nonfunctional. This problem may be reduced to certain extent by overexpressing the MAP together with the recombinant protein.

Eukaryotic MAPs have been purified and characterized from S. cerevisiae and porcine liver 8, 9). All bacterial and eukaryotic MAPs known to date are cobalt-dependent metallopeptidases, and they share similar substrate specificity. Favorable peptide substrates for MAPs possess an $NH_2$-terminal methionine followed by a small and uncharged residue, which is in general agreement with the specificities of MAPs predicted by the in vivo studies. Moreover, the X-ray structure of E. coli MAP was recently determined to 2.4 A resolution (10). This bacterial MAP contains two cobalt ions in the active site and it appears to represent a new class of proteolytic enzymes. The genes encoding MAPs from E. coli, S. typhimurium and S. cerevisiae have been cloned and sequenced (3, 5, 11, 12).

Eukaryotic initiation factor-2 (eIF-2) comprises three subunits: α,β and γ. In mammals, there are several eIF-2 kinases, such as double-stranded RNA-activated inhibitor (dsI) and heme regulated inhibitor, which can specifically phosphorylate the alpha-subunit of eIF-2 under certain physiological conditions. Phosphorylation of eIF-2 alpha-subunit inactivates the function of eIF-2 and thereby inhibits protein synthesis. This regulatory mechanism is widely used in animal cells under nutritional deprivation, heat shock, and viral infection. An eIF-2 associated glycoprotein (p67) has been isolated from rabbit reticulocyte lysates (15). The glycoprotein (p67) promotes protein synthesis in the presence of active eIF-2 kinase by protecting the eIF-2 α-subunit from eIF-2 kinase-catalyzed phosphorylation.

This invention relates to cloning of a nucleotide sequence which encodes a protein that palys an essential role in the removal of the initiator methionine and in the regulation of protein synthesis in eukaryotes.

SUMMARY OF THE INVENTION

An object of the instant invention is providing a nucleotide sequence (SEQ. ID. 1) which encodes for a protein having amino acid sequence substantially similar to eukaryotic initiation factor-2 (eIF-2) associated glycoprotein (p67) and the encoded protein is also capable of removing N-terminal methionine from proteins. The encoded protein having amino acid sequence which is 95% similar to rat initiation factor associated glycoprotein (p67). The protein encoded by the nucleotide sequence may facilitate the function of an eukaryotic initiation factor and thus plays a regulatory role in regulation of protein synthesis. The encoded protein also acts as methionine aminopeptidase that removes the $NH_2$-methionine during protein synthesis. The removal of N-terminal methionine is essential for subsequent modification of proteins, such as N-myristolylation, which is essential for regulation of signal transduction, protein targeting and cancer cell growth in animal system. Therefore, examining the expression of the protein molecule encoded by the nucleotide sequence or the corresponding RNA will provide important information about protein synthesis and other cellular functions. Thus the nucleotide sequence may also be used for monitoring synthesis of methionine aminopeptidase and/or eIF-2 associated glycoprotein (p67).

Yet another object of the instant invention is a method of facilitating protein synthesis in protein expression and/or synthesizing systems. Said nucleotide sequence may be provided to protein synthesizing system to facilitate synthesis of a desired protein by overexpressing the protein encoded by said nucleotide sequence. The encoded protein may facilitate protein synthesis by protecting the eIF-2 from phosphorylation and may also remove N-terminal methionine from the desired protein. The protein synthesizing system may be in-vitro, in-vivo, recombinant or any other system that may become available in future. This discovery also establishes that methionine aminopeptidase and eIF-2 associated glycoprotein (p67) are substantially one and the same protein and thus providing cellular system with the cloned nucleotide sequence will serve both cellular functions.

BRIEF DESCRIPTION OF THE DRAWINGS

FIG. 1. Nucleotide (SEQ ID NO:1), coding region in all upper case letters (SEQ ID NO:2) and deduced amino acid sequence (SEQ ID NO:3) of human methionine aminopeptidase cDNA. The nucleotides are numbered from 5' to 3' on the left margin. The amino acids are numbered at the right margin.

FIG. 2. Alignment of the protein sequences of rat p67 and human methionine aminopeptidase.

DESCRIPTION OF THE INVENTION

The nucleotide of the instant invention was cloned from human liver tissue. CDNA of yeast methionine aminopeptidase-2 was used as the hybridization probe. The positive plaques were further purified using the sequence information from the rat p67 gene (16). The p67 gene sequence was amplified in a region where it shows homology with the yeast methionine aminopeptidase-2 gene. An approximately 480 bp was amplified. The plaques producing 480 bp PCR products were the positive clones. The cloned nucleotide sequence encoded a protein which has 95% amino acid sequence similarity with the rat eIF-2 associated glycoprotein p67 and also catalyzed the removal of $NH_2$-methionine from protein. Based on the exceptionally high sequence similarity (95%) of the encoded protein with the p67 protein as well as its methionine amino peptidase activity it is concluded that the encoded protein have at least two cellular functions, the encoded protein may facilitate protein synthesis by protecting the eIF-2 from phosphorylation and may also removed N-terminal methionine from proteins and prepare the proteins for critical cellular functions. In a protein expression system, the introduction of the cloned nucleotide sequence will facilitate protein synthesis.

The invention is further explained with reference to the following example.

EXAMPLE

To clone the nucleotide sequence, the cDNA of yeast methionine aminopeptidase-2 (12) was used as the hybridization probe and screened a human liver Uni-ZAP cDNA library, purchased from Stratagene (La Jolla, Calif. USA). Fifteen positives were obtained from ~1×10⁶ plaques. For plaque purifications, polymerase chain reaction approach was employed, using two oligonucleotide primers, 5'-GCCATTCAAGAAGTTATGGAGTCCTATGAAGTGGA-3' (forward) and 5'-TAGGTATGTTCAAACTGTGCTGTGTATGATCC-3' (backward), (SEQ ID NO: 5) based on the sequence of the rat p67 gene (16) that is conserved between the rat p67 and yeast methionine aminopeptidase 2. Only one PCR product with the expected size of ~480 bp was amplified from some of the positive plaques. Those plaques that produced the 480 bp PCR products were considered to be real positives and further analyzed. The phage DNA from each positive was converted to phagmid vector according to the manufacturer's protocol (Stratagene, La Jolla, Calif. USA). The insert size of the plasmid from each clone was analyzed after Xho I/EcoRI digestion. One clone with the longest insert (~2.0 kb) was used for sequencing. Two sets of nested deletions were generated by using Promega's Erase-a-base kit (Promega, Madison, Mich. USA) from both directions and were sequenced by the dideoxy method using the Sequenase kit from US Biochemical Corp. As shown in FIG. 1, the cloned cDNA insert of 1927 nucleotides contains a single open reading from initiating with an ATG codon at nucleotide position 35–37 and terminating with a TAA stop codon at position 1469–1471. The sequence surrounding the initiating ATG codon, AACATGG, fits well with the consensus established by Kozak (13). In the 3'-untranslated region, there is a putative polyadenylation signal sequence, AATAAA, located 16 nucleotides upstream of the poly(A) tract. The open reading frame encodes a protein 478 amino acids with pI of 5.64 and a calculated molecular mass of 52,891. Amino acid sequence comparison revealed that the sequence of human proteins shares 92% identity and 95% similarity with that of rat p67, and 52% identity with that of yeast methionine aminopeptidase-2. It is worth noting that the amino acid sequence is highly conserved between human methionine aminopeptidase and rat p67 until residue 464, and the discontinuity in homology is caused by a single insertion in the human gene (or a single deletion in the rat. gene) with unknown reasons.

The conservation between human methionine aminopeptidase and rat p67 is shown in FIG. 2. The 92% identity mentioned above is reflected in the identical amino acids in human methionine aminopeptidase and rat p67 as shown by vertical bars. The 95% similarity is reflected in the total of identical amino acids and similar or conserved amino acids as identified by vertical bars for identical amino acids and single or double dots for conserved amino acids. Such conserved amino acids substitutions as shown an FIG. 2 are as follows: alanine-valine, serine-alanine, phenylalanine-serine, glycine-serine, threonine-alanine, alanine-proline, glutamine-glutamic acid, lysine-arginine, glutamic acid-aspartic acid, arginine-lysine, isoleucine-threonine, proline-glutamine, proline-threonine, valine-cysteine, lysine-glutamic acid, leucine-valine, and glutamic acid-glycine.

Figure 3:
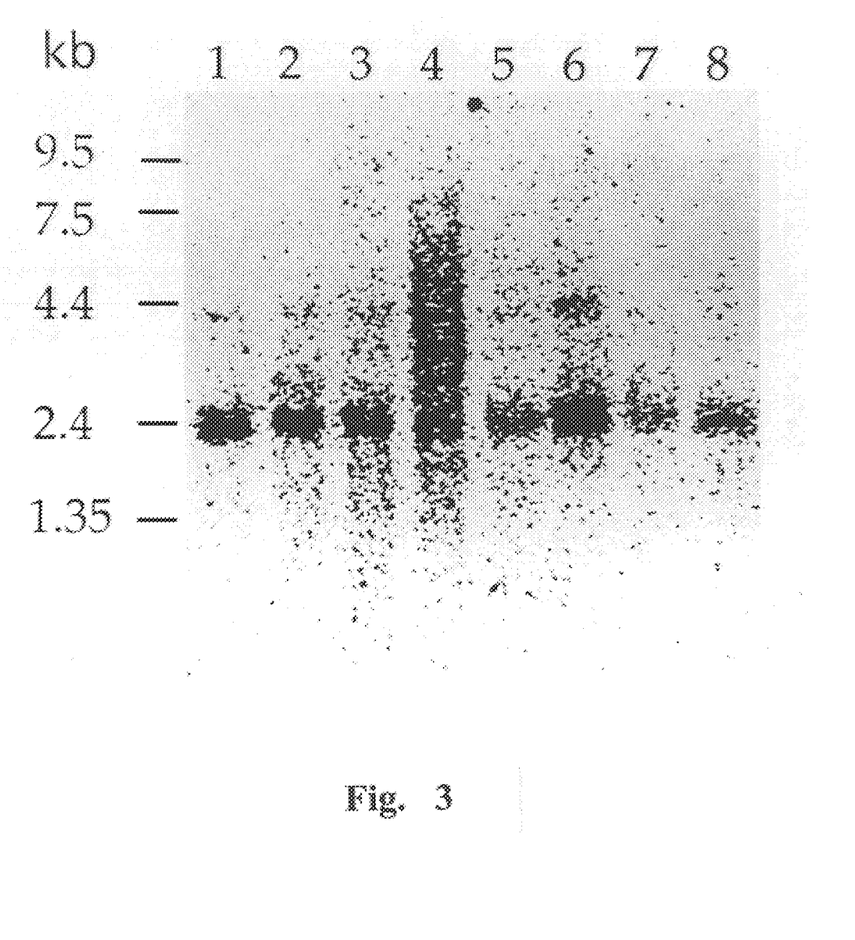
FIG. 3. Hybridization of human multiple tissue northern blot from Clontech (Palo Alto, Calif. USA) with the human methionine aminopeptidase cDNA probe. Each lane contains approximately 2 µg of pure PolyA+RNA isolated from the following human tissues: Lane 1: Heart. Lane 2: Brain. Lane 3: Placenta. Lane 4: Lung. Lane 5: Liver. Lane 6: Skeletal muscle. Lane 7: Kidney. Lane 8: Pancrease. After a high stringency wash (0.2× SSC at 60° C.), the blot was analyzed by a phosphoimager.

The human methionine aminopeptidase, like yeast methionine aminopeptidase 2 and rat 67, contains highly charged amino acids at the N-terminal region. Human eIF-2β and yeast protein Sui3 also contain similar polylysine blocks which have been postulated to be involved in protein/protein or protein/nucleic acid interactions. Furthermore, it was found that the human protein shares significant 22% identity with yeast methionine aminopeptidase 1 and the bacterial methionine aminopeptidases (MAPs). Recently, Bazan, J. F. et al. reported that the rat p67 may share a similar folding with bacterial MAP, aminopeptidase-P, prolidases and creatinases (14). They also found that the five residues involved in metal binding, identified by Roderick and Matthews (10), are strictly conserved in all four methionine aminopeptidases, in three aminopeptidase-P, in three prolidases and in rat p67 with only one exception that the site 235 in E. coli MAP and in other related enzymes in Glu, whereas its corresponding residue in rat p67 s His. They predicted that p67 may be a metalloprotease which can modify and inactivate the attacking eIF-2 kinases (14). This hypothesis differs from the observations of Gupta and coworkers who showed that the eIF-2 kinase was still active in the presence of rat p67 under their assaying conditions (15, 16). This finding that the human and the rat proteins are homologous to the second methionine aminopeptidase (MAP2) from S. cerevisia suggests that p67 is very likely to be a bifunctional protein. To evaluate the tissue distribution and the size of the mRNA of p67, a northern blot analysis was carried out using $^{32}$P-labeled cDNA of human methionine aminopeptidase 2 to probe a RNA blot from Clontech (Palo Alto, Calif. USA). FIG. 3 indicates that the gene of human methionine aminopeptidase 2 is expressed in all tested human tissues, and the size of the corresponding polyA-RNA (~2.1 kb) is close to the size of our cloned CDNA. The extremely high identity between the human methionine aminopeptidase 2 and rat p67 sequences suggests that the function of this protein is fundamentally important and highly conserved.

To determine whether this human protein is indeed a methionine aminopeptidase, this human cloned gene was expressed in insect cells using the baculovirus expression system. The recombinant human protein was purified to homogeneity and used for enzyme assay. It was found that this human protein indeed has methionine aminopeptidase activity, indicating that this human protein has dual functions, i.e. a methionine aminopeptidase-like function in amino-terminal processing and a p67-like function in regulation of protein synthesis.

Reference

All references cited herein are incorporated herein by reference in entirety.
1. Ball L A, Kaesberg P (1973) *J. Mol. Biol.* 79:531–537
2. Moerschell R P, Hosokawa Y, Tsunasawa S, Sherman F (1990) *J. Biol. Chem* 265:19638–19643

3. Ben-Bassat A, Bauer K, Chang S Y, Myambo K, Boosman A, Chang S (1987) *J. Bacteriol.* 169:751–757
4. Huang S, Elliott R C, Liu P S, Koduri R K, Weickmann J L, Lee J H, Blair L C, Ghosh-Dastidar P, Bradshaw R A, Bryan K M, et al (1987) *Biochemistry* 26:8242–8246
5. Miller C G, Strauch K L, Kukral A M, Miller J L, Wingfield P T, Mazzei G J, Werlen R C, Graber P, Movva N R (1987) *Proc. Natl. Acad Sci USA* 84:2718–2722
6. Gordon J I, Duronio R J, Rudnick D A, Adams S P, Gokel G W (1991) *J. Biol. Chem.* 266:8647–8650
7. Duronio R J, Towler D A, Heuckeroth R O, Gordon J I (1989) *Science* 243:796–800
8. Chang Y H, Teichert U, Smith J A (1990) *J. Biol. Chem.* 265:19892–19897
9. Kendall R L, Bradshaw R A (1992) *J. Biol. Chem.* 267:20667–20673
10. Roderick S L, Matthews B W (1993) *Biochemistry* 32:3907–3912
11. Chang Y H, Teichet U, Smith J A (1992) *J. Biol. Chem.* 267–8007–11
12. Li X, Chang Y H (1995) *Proc. Natl. Acad Sci* 92:12375–12361
13. Kozak M (1991) *J. Biol. Chem.* 26:19867–19870
14. Bazan J F, Weaver L H, Roderick S., Huber R and Mathew B W (1994)*Proc. Natl. Acad Sci USA* 91:2473–2477
15. Ray M K, Chakarabort A, Datta B, Chattopadhyay A, Saha D, Bose A, Kinzy T G, Wu S, Hileman R E, Merrick W C and Gupta N K (1993) *Biochemistry* 32:5151–5159
16. Wu S, Gupta S, Chatterjee N, Hileman R E, Kinzy T G, Denslow N D, Merrick W C, Chakarabarti D, Osterman J C and Gupta N K (1993)*J. Biol. Chem.* 268:10796–10801

---

What I claim is:

1. An isolated polypeptide comprising a methionine aminopeptidase having a sequence as set forth in SEQ ID NO:3 or a conservatively substituted variant thereof.

2. The isolated polypeptide according to claim 1 comprising a human methionine aminopeptidase polypeptide.

3. The isolated polypeptide according to claim 1 comprising SEQ ID NO:3.

4. The isolated polypeptide according to claim 1 comprising a conservatively substituted variant of SEQ ID NO: 3.

5. The isolated polypeptide according to claim 1 consisting of SEQ ID NO:3.

6. The isolated polypeptide according to claim 1 consisting of a conservatively substituted variant of SEQ ID NO:3.

7. The isolated polypeptide according to claim 2 consisting of a methionine aminopeptidase of 478 contiguous amino acids wherein the methionine aminopeptidase is at least 92% identical to SEQ ID NO:3.

8. An isolated polypeptide comprising an enzymatically active fragment of the protein described in SEQ. ID NO:3.

9. An isolated polypeptide comprising a methionine aminopeptidase of 478 contiguous amino acids wherein the methionine aminopeptidase is at least 92% identical to SEQ ID NO:3.

10. The isolated polypeptide of claim 9 wherein the methionine aminopeptidase has at least a 95% similarity to SEQ ID NO:3.

11. An isolated polypeptide comprising a methionine aminopeptidase which is encoded by a polynucleotide the complement of which hybridizes with SEQ ID NO:1 or SEQ ID NO:2 under high stringency conditions, or a conservatively substituted variant of said methionine aminopeptidase.

12. An isolated polypeptide of claim 11 comprising a human methionine aminopeptidase.

* * * * *

UNITED STATES PATENT AND TRADEMARK OFFICE
CERTIFICATE OF CORRECTION

PATENT NO.  : 5,888,796
DATED       : March 30, 1999
INVENTOR(S) : Yie-Hwa Chang It is certified that error appears in the above-identified patent and that said Letters Patent is hereby corrected as shown below:

Claim 8,
Should be renumbered as Claim -- 7 --;

Claim 9,
Should be renumbered as Claim -- 8 --;

Claim 10,
Should be renumbered as Claim -- 9 -- with a dependency on Claim -- 8 --; and Claim 7,
Should be renumbered as Claim -- 10 -- with a dependency on Claim -- 9 --.

Signed and Sealed this

Thirtieth Day of October, 2001

*Attest:*

*Nicholas P. Godici*

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1927 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

```
CTCTGTCTCA  TTCCCTCGCG  CTCTCTCGGG  CAACATGGCG  GGTGTGGAGG  AGGTAGCGGC      60

CTCCGGGAGC  CACCTGAATG  GCGACCTGGA  TCCAGACGAC  AGGGAAGAAG  GAGCTGCCTC     120

TACGGCTGAG  GAAGCAGCCA  AGAAAAAAAG  ACGAAAGAAG  AAGAAGAGCA  AAGGGCCTTC     180

TGCAGCAGGG  GAACAGGAAC  CTGATAAAGA  ATCAGGAGCC  TCAGTGGATG  AAGTAGCAAG     240

ACAGTTGGAA  AGATCAGCAT  TGGAAGATAA  AGAAAGAGAT  GAAGATGATG  AAGATGGAGA     300

TGGCGATGGA  GATGGAGCAA  CTGGAAAGAA  GAAGAAAAAG  AAGAAGAAGA  AGAGAGGACC     360

AAAAGTTCAA  ACAGACCCTC  CCTCAGTTCC  AATATGTGAC  CTGTATCCTA  ATGGTGTATT     420

TCCCAAAGGA  CAAGAATGCG  AATACCCACC  CACACAAGAT  GGGCGAACAG  CTGCTTGGAG     480

AACTACAAGT  GAAGAAAAGA  AAGCATTAGA  TCAGGCAAGT  GAAGAGATTT  GGAATGATTT     540

TCGAGAAGCT  GCAGAAGCAC  ATCGACAAGT  TAGAAAATAC  GTAATGAGCT  GGATCAAGCC     600

TGGGATGACA  ATGATAGAAA  TCTGTGAAAA  GTTGGAAGAC  TGTTCACGCA  AGTTAATAAA     660

AGAGAATGGA  TTAAATGCAG  GCCTGGCATT  TCCTACTGGA  TGTTCTCTCA  ATAATTGTGC     720

TGCCCATTAT  ACTCCCAATG  CCGGTGACAC  AACAGTATTA  CAGTATGATG  ACATCTGTAA     780

AATAGACTTT  GGAACACATA  TAAGTGGTAG  GATTATTGAC  TGTGCTTTTA  CTGTCACTTT     840

TAATCCCAAA  TATGATACGT  TATTAAAAGC  TGTAAAAGAT  GCTACTAACA  CTGGAATAAA     900

GTGTGCTGGA  ATTGATGTTC  GTCTGTGTGA  TGTTGGTGAG  GCCATCCAAG  AAGTTATGGA     960

GTCCTATGAA  GTTGAAATAG  ATGGGAAGAC  ATATCAAGTG  AAACCAATCC  GTAATCTAAA    1020

TGGACATTCA  ATTGGGCAAT  ATAGAATACA  TGCTGGAAAA  ACAGTGCCGA  TTGTGAAAGG    1080

AGGGGAGGCA  ACAAGAATGG  AGGAAGGAGA  AGTATATGCA  ATTGAAACCT  TTGGTAGTAC    1140

AGGAAAAGGT  GTTGTTCATG  ATGATATGGA  ATGTTCACAT  TACATGAAAA  ATTTTGATGT    1200
```

```
TGGACATGTG  CCAATAAGGC  TTCCAAGAAC  AAAACACTTG  TTAAATGTCA  TCAATGAAAA   1260
CTTTGGAACC  CTTGCCTTCT  GCCGCAGATG  GCTGGATCGC  TTGGGAGAAA  GTAAATACTT   1320
GATGGCTCTG  AAGAATCTGT  GTGACTTGGG  CATTGTAGAT  CCATATCCAC  CATTATGTGA   1380
CATTAAAGGA  TCATATACAG  CGCAATTTGA  ACATACCATC  CTGTTGCGTC  AACATGTAA    1440
AGAAGTTGTC  AGCAGAGGAG  ATGACTATTA  AACTTAGTCC  AAAGCCACCT  CAACACCTTT   1500
ATTTTCTGAG  CTTTGTTGGA  AAACATGATA  CCAGAATTAA  TTTGCCACAT  GTTGTCTGTT   1560
TTAACAGTGG  ACCCATGTAA  TACTTTTATC  CATGTTTAAA  AAGAAGGAAT  TTGGACAAAG   1620
GCAAACCGTC  TAATGTAATT  AACCAACGAA  AAAGCTTTCC  GGACTTTTAA  ATGCTAACTG   1680
TTTTTCCCCT  TCCTGTCTAG  GAAAATGCTA  TAAAGCTCAA  ATTAGTTAGG  AATGACTTAT   1740
ACGTTTTGTT  TTGAATACCT  AAGAGATACT  TTTTGGATAT  TTATATTGCC  ATATTCTTAC   1800
TTGAATGCTT  TGAATGACTA  CATCCAGTTC  TGCACCTATA  CCCTCTGGTG  TTGCTTTTA    1860
ACCTTCCTGG  AATCCATTTC  TAAAAAATAA  AGACATTTTC  AGATCTGAAA  AAAAAAAAA    1920
AAAAAAA                                                                  1927
```

(2) INFORMATION FOR SEQ ID NO:2:

(i) SEQUENCE CHARACTERISTICS:
        (A) LENGTH: 1434 base pairs
        (B) TYPE: nucleic acid
        (C) STRANDEDNESS: single
        (D) TOPOLOGY: linear     (ii) MOLECULE TYPE: cDNA     (xi) SEQUENCE DESCRIPTION: SEQ ID NO:2:

```
ATGGCGGGTG  TGGAGGAGGT  AGCGGCCTCC  GGGAGCCACC  TGAATGGCGA  CCTGGATCCA    60
GACGACAGGG  AAGAAGGAGC  TGCCTCTACG  GCTGAGGAAG  CAGCCAAGAA  AAAAAGACGA   120
AAGAAGAAGA  AGAGCAAAGG  GCCTTCTGCA  GCAGGGGAAC  AGGAACCTGA  TAAAGAATCA   180
GGAGCCTCAG  TGGATGAAGT  AGCAAGACAG  TTGGAAAGAT  CAGCATTGGA  AGATAAAGAA   240
AGAGATGAAG  ATGATGAAGA  TGGAGATGGC  GATGGAGATG  GAGCAACTGG  AAAGAAGAAG   300
AAAAGAAGA   AGAAGAAGAG  AGGACCAAAA  GTTCAAACAG  ACCCTCCCTC  AGTTCCAATA   360
TGTGACCTGT  ATCCTAATGG  TGTATTTCCC  AAAGGACAAG  AATGCGAATA  CCCACCCACA   420
CAAGATGGGC  GAACAGCTGC  TTGGAGAACT  ACAAGTGAAG  AAAAGAAAGC  ATTAGATCAG   480
GCAAGTGAAG  AGATTTGGAA  TGATTTTCGA  GAAGCTGCAG  AAGCACATCG  ACAAGTTAGA   540
AAATACGTAA  TGAGCTGGAT  CAAGCCTGGG  ATGACAATGA  TAGAAATCTG  TGAAAAGTTG   600
GAAGACTGTT  CACGCAAGTT  AATAAAGAG   AATGGATTAA  ATGCAGGCCT  GGCATTTCCT   660
ACTGGATGTT  CTCTCAATAA  TTGTGCTGCC  CATTATACTC  CCAATGCCGG  TGACACAACA   720
GTATTACAGT  ATGATGACAT  CTGTAAAATA  GACTTTGGAA  CACATATAAG  TGGTAGGATT   780
ATTGACTGTG  CTTTTACTGT  CACTTTTAAT  CCCAAATATG  ATACGTTATT  AAAAGCTGTA   840
AAAGATGCTA  CTAACACTGG  AATAAAGTGT  GCTGGAATTG  ATGTTCGTCT  GTGTGATGTT   900
GGTGAGGCCA  TCCAAGAAGT  TATGGAGTCC  TATGAAGTTG  AAATAGATGG  AAGACATAT    960
CAAGTGAAAC  CAATCCGTAA  TCTAAATGGA  CATTCAATTG  GGCAATATAG  AATACATGCT  1020
GGAAAAACAG  TGCCGATTGT  GAAAGGAGGG  GAGGCAACAA  GAATGGAGGA  AGGAGAAGTA  1080
TATGCAATTG  AAACCTTTGG  TAGTACAGGA  AAAGGTGTTG  TTCATGATGA  TATGGAATGT  1140
TCACATTACA  TGAAAAATTT  TGATGTTGGA  CATGTGCCAA  TAAGGCTTCC  AAGAACAAAA  1200
```

CACTTGTTAA ATGTCATCAA TGAAAACTTT GGAACCCTTG CCTTCTGCCG CAGATGGCTG    1260

GATCGCTTGG GAGAAAGTAA ATACTTGATG GCTCTGAAGA ATCTGTGTGA CTTGGGCATT    1320

GTAGATCCAT ATCCACCATT ATGTGACATT AAAGGATCAT ATACAGCGCA ATTTGAACAT    1380

ACCATCCTGT TGCGTCCAAC ATGTAAAGAA GTTGTCAGCA GAGGAGATGA CTAT          1434

( 2 ) INFORMATION FOR SEQ ID NO:3:

( i ) SEQUENCE CHARACTERISTICS:
        ( A ) LENGTH: 478 amino acids
        ( B ) TYPE: amino acid
        ( C ) STRANDEDNESS:
        ( D ) TOPOLOGY: linear     ( i i ) MOLECULE TYPE: protein     ( x i ) SEQUENCE DESCRIPTION: SEQ ID NO:3:

```
Met Ala Gly Val Glu Val Ala Ala Ser Gly Ser His Leu Asn Gly
 1               5                  10                  15

Asp Leu Asp Pro Asp Asp Arg Glu Glu Gly Ala Ala Ser Thr Ala Glu
                20                  25                  30

Glu Ala Ala Lys Lys Lys Arg Arg Lys Lys Lys Lys Ser Lys Gly Pro
                35                  40                  45

Ser Ala Ala Gly Glu Gln Glu Pro Asp Lys Glu Ser Gly Ala Ser Val
        50                  55                  60

Asp Glu Val Ala Arg Gln Leu Glu Arg Ser Ala Leu Glu Asp Lys Glu
65                  70                  75                  80

Arg Asp Glu Asp Asp Glu Asp Gly Asp Gly Asp Gly Asp Gly Ala Thr
                    85                  90                  95

Gly Lys Lys Lys Lys Lys Lys Lys Lys Arg Gly Pro Lys Val Gln
                    100                 105                 110

Thr Asp Pro Pro Ser Val Pro Ile Cys Asp Leu Tyr Pro Asn Gly Val
                115                 120                 125

Phe Pro Lys Gly Gln Glu Cys Glu Tyr Pro Pro Thr Gln Asp Gly Arg
        130                 135                 140

Thr Ala Ala Trp Arg Thr Thr Ser Glu Glu Lys Lys Ala Leu Asp Gln
145                 150                 155                 160

Ala Ser Glu Glu Ile Trp Asn Asp Phe Arg Glu Ala Ala Glu Ala His
                    165                 170                 175

Arg Gln Val Arg Lys Tyr Val Met Ser Trp Ile Lys Pro Gly Met Thr
                    180                 185                 190

Met Ile Glu Ile Cys Glu Lys Leu Glu Asp Cys Ser Arg Lys Leu Ile
                195                 200                 205

Lys Glu Asn Gly Leu Asn Ala Gly Leu Ala Phe Pro Thr Gly Cys Ser
        210                 215                 220

Leu Asn Asn Cys Ala Ala His Tyr Thr Pro Asn Ala Gly Asp Thr Thr
225                 230                 235                 240

Val Leu Gln Tyr Asp Asp Ile Cys Lys Ile Asp Phe Gly Thr His Ile
                    245                 250                 255

Ser Gly Arg Ile Ile Asp Cys Ala Phe Thr Val Thr Phe Asn Pro Lys
                    260                 265                 270

Tyr Asp Thr Leu Leu Lys Ala Val Lys Asp Ala Thr Asn Thr Gly Ile
                275                 280                 285

Lys Val Ala Gly Ile Asp Val Arg Leu Cys Asp Val Gly Glu Ala Ile
            290                 295                 300

Gln Glu Val Met Glu Ser Tyr Glu Val Glu Ile Asp Gly Lys Thr Tyr
305                 310                 315                 320
```

```
Gln  Val  Lys  Pro  Ile  Arg  Asn  Leu  Asn  Gly  His  Ser  Ile  Gly  Gln  Tyr
                    325                      330                     335

Arg  Ile  His  Ala  Gly  Lys  Thr  Val  Pro  Ile  Val  Lys  Gly  Gly  Glu  Ala
               340                      345                     350

Thr  Arg  Met  Glu  Glu  Gly  Glu  Val  Tyr  Ala  Ile  Glu  Thr  Phe  Gly  Ser
          355                      360                     365

Thr  Gly  Lys  Gly  Val  Val  His  Asp  Asp  Met  Glu  Cys  Ser  His  Tyr  Met
     370                      375                     380

Lys  Asn  Phe  Asp  Val  Gly  His  Val  Pro  Ile  Arg  Leu  Pro  Arg  Thr  Lys
385                      390                     395                          400

His  Leu  Leu  Asn  Val  Ile  Asn  Glu  Asn  Phe  Gly  Thr  Leu  Ala  Phe  Cys
                    405                      410                     415

Arg  Arg  Trp  Leu  Asp  Arg  Leu  Gly  Glu  Ser  Lys  Tyr  Leu  Met  Ala  Leu
               420                      425                     430

Lys  Asn  Leu  Cys  Asp  Leu  Gly  Ile  Val  Asp  Pro  Tyr  Pro  Pro  Leu  Cys
          435                      440                     445

Asp  Ile  Lys  Gly  Ser  Tyr  Thr  Ala  Gln  Phe  Glu  His  Thr  Ile  Leu  Leu
     450                      455                     460

Arg  Pro  Thr  Cys  Lys  Glu  Val  Val  Ser  Arg  Gly  Asp  Asp  Tyr
465                      470                     475
```

( 2 ) INFORMATION FOR SEQ ID NO:4:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

GCCATTCAAG AAGTTATGGA GTCCTATGAA GTGGA                                       35

( 2 ) INFORMATION FOR SEQ ID NO:5:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

TAGGTATGTT CAAACTGTGC TGTGTATGAT CC                                          32